United States Patent
Cassels et al.

(10) Patent No.: US 7,094,883 B1
(45) Date of Patent: Aug. 22, 2006

(54) **MONOCLONAL ANTIBODY WHICH AGGLUTINATES *E. COLI* HAVING THE CS4-CFA/I FAMILY PROTEIN**

(75) Inventors: Frederick Cassels, Ellicott City, MD (US); Andrew Lees, Silver Spring, MD (US); Richard Schuman, North Potomac, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 08/905,046

(22) Filed: Aug. 1, 1997

Related U.S. Application Data
(60) Provisional application No. 60/023,075, filed on Aug. 2, 1996.

(51) Int. Cl.
*C07K 16/00* (2006.01)
*A61K 39/40* (2006.01)
*A61K 39/395* (2006.01)

(52) U.S. Cl. ................. 530/388.4; 530/388.2; 530/388.1; 530/387.9; 530/350; 530/300; 424/139.1; 424/141.1; 424/150.1; 424/130.1; 424/164.1

(58) Field of Classification Search ............. 530/388.4, 530/388.1, 388.2, 387.1, 387.9, 350, 300, 530/328, 825, 820; 424/139.1, 141.1, 150.1, 424/130.1, 164.1; 435/7.1, 7.2, 7.32, 7.37, 435/7.92, 29; 436/548, 546, 519, 800
See application file for complete search history.

(56) References Cited

U.S. PATENT DOCUMENTS 5,914,114 A * 6/1999 Cassels .................... 424/241.1
6,045,799 A * 4/2000 Reeves et al. ........... 424/192.1

FOREIGN PATENT DOCUMENTS

WO WO 9638171 * 12/1996

* cited by examiner

*Primary Examiner*—S. Devi
(74) *Attorney, Agent, or Firm*—Elizabeth Arwine; John Francis Moran; Charles H. Harris

(57) ABSTRACT

A monoclonal antibody to a consensus peptide of the formula:

V E K K N I T V T A S V D P T I D L L Q A D G S A L P - S A V A L T Y S P A (SEQ ID NO. 1) is described.

The monoclonal antibody of the invention binds exclusively to the sequence SAVALTYS (SEQ ID NO. 2) and has use as a diagnostic and for prophylaxis against illness arising from *E. coli* which produce the CS4-CFA/I family of proteins and for treatment of disease arising therefrom.

7 Claims, No Drawings

```
                          SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
            (A) LENGTH: 36 amino acids
            (B) TYPE: amino acid
            (C) STRANDEDNESS: single
            (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
            (A) ORGANISM: E. COLI
            (B) STRAIN: CS4-CFA/I (xi) SEQUENCE DESCRIPTION: SEQ ID NO:1:

Val Glu Lys Asn Ile Thr Val Thr Ala Ser Val Asp Pro Thr Ile Asp
1               5                   10                  15

Leu Leu Gln Ala Asp Gly Ser Ala Leu Pro Ser Ala Val Ala Leu Thr
                20                  25                  30

Tyr Ser Pro Ala
        35

(2) INFORMATION FOR SEQ ID NO:2:

(i) SEQUENCE CHARACTERISTICS:
            (A) LENGTH: 8 amino acids
            (B) TYPE: amino acid
            (C) STRANDEDNESS: single
            (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
            (A) ORGANISM: E. COLI
            (B) STRAIN: CS4-CFA/I (xi) SEQUENCE DESCRIPTION: SEQ ID NO:2:
```

```
-continued

Ser Ala Val Ala Leu Thr Tyr Ser
1               5

(2) INFORMATION FOR SEQ ID NO:3:

(i) SEQUENCE CHARACTERISTICS:
        (A) LENGTH: 37 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: E. COLI
        (B) STRAIN: CS4-CFA/I (xi) SEQUENCE DESCRIPTION: SEQ ID NO:3:

Cys Val Glu Lys Asn Ile Thr Val Thr Ala Ser Val Asp Pro Thr Ile
1               5                   10                  15

Asp Leu Leu Gln Ala Asp Gly Ser Ala Leu Pro Ser Ala Val Ala Leu
            20                  25                  30

Thr Tyr Ser Pro Ala
            35
```

MONOCLONAL ANTIBODY WHICH AGGLUTINATES *E. COLI* HAVING THE CS4-CFA/I FAMILY PROTEIN

The application takes priority from Provisional Patent Application 60/023,075 filed Aug. 2, 1996.

FIELD OF THE INVENTION

This invention relates to a monoclonal antibody to a consensus peptide of the formula:
VEKNITVTASVDPTIDLLQADGSALPSAVALTYSPA (SEQ. ID. NO. 1)
The monoclonal antibody of the invention binds exclusively to the sequence SAVALTYS (SEQ. ID. NO. 2).

BACKGROUND OF THE INVENTION

The effect of *E. coli* in mammals is dependent on the particular strain of organism. Many beneficial *E. coli* are present in the intestines. Since the initial association of *E. coli* with diarrheal illness, five categories of diarrheagenic *E. coli* have been identified and are presently recognized: enterotoxigenic (ETEC), enteropathogenic (EPEC), enterohemorrhagic (EHEC), enteroaggregative (EAggEC), and enteroinvasive (EIEC). These categories are grouped according to characteristic virulence properties, such as elaboration of toxins and colonization factors and/or by specific types of interactions with intestinal epithelial cells. ETEC are the most common of the diarrheagenic *E. coli* and pose the greatest risk to travelers. *E. coli* of the family CS4-CFA/I are some of the more common enterotoxigenic *E. coli*. There is need for vaccines which are specific against this class of *E. coli* that give rise to antibodies that cross-react with and cross-protect against the more common members of the CS4-CFA/I family. Six members of this family of ETEC fimbrial proteins are CFA/I, CS1, CS2, CS4, CS17 and PCF 0166. ETEC are responsible for high infant mortality in developing countries, with an estimate that almost 800,000 deaths per year due to these organisms. These organisms also cause illness in adult travelers to regions where the disease is endemic.

Colonization factor antigens (CFA) of ETEC are important in the initial step of colonization and adherence of the bacterium to intestinal epithelia. In epidemiological studies of adults and children with diarrhea, CFA/I is found in a large percentage of morbidity attributed to ETEC. The CFA/I is present on the surfaces of bacteria in the form of pili (fimbriae), which are rigid, 7 nm diameter protein fibers composed of repeating pilin subunits. The CFA/I antigens promote mannose-resistant attachment to human brush borders with an apparent sialic acid sensitivity.

A study of proteins in *E. coli* belonging to the CS4-CFA/I family resulted in the finding that the N-terminal region of the protein maintains a high degree of sequence identity between members of this group. Immunological evidence shows that cross-reaction exists between members of the family CS4-CFA/I.

Cassels, et al. have identified a consensus peptide of 36 amino acids which acts as an immunogen raising antibodies against the proteins of all members of the *E. coli* family CS4-CFA/I. The region of the protein represented in the subunit encompasses known linear B- and T-cell epitopes of CFA/I. The consensus peptide has a high level of homology to strains bearing six different colonization factors. The consensus peptide is of the formula:
VEKNITVTASVDPTIDLLQADGSALPSAVALTYSPA (SEQ. ID. NO. 1)

DESCRIPTION OF THE INVENTION

It is the purpose of this invention to identify a monoclonal antibody raised to the consensus peptide of Cassels and which will agglutinate all bacteria bearing CS4-CFA/I family proteins.

Preparation of the Immunogen:

A: Iodoacetylation of tetanus toxoid:

To 0.64 ml of a composition containing 18.9 mg/ml (12 mg) of tetanus toxoid (TT) (obtained from SmithKline Beecham) was added 5×HEPES buffer (75 µl of 0.75 M HEPES, 5 mM EDTA, pH 7.3). The TT was labeled with a 40 fold molar excess of N-hydroxysuccinimidyl iodoacetate (32 µl of 0.1 mM in dimethyl-formamide). After two hours, the protein was desalted on 2 P6 cartridges (BioRad) in series, equilibrated with HEPES buffer (0.15M HEPES, 1 mM EDTA, pH 7.3). The void volume fraction was concentrated to about 0.7 ml using a Macrosep™50 device (Filtron Corp).

B: Reduction of peptide:

About 10 mg of peptide consensus peptide of the formula
CVEKNITVTASVDPTIDLLQADGSALP-SAVALTYSPA (SEQ. ID. No. 3)
was solubilized in 1.1 ml HEPES buffer containing 100 µl acetonitrile and reduced by the addition of solid dithiothreitol to a final concentration of 0.5 M. After 1 hour the peptide was desalted in two parts on a 1×50 cm G10 column (Pharmacia), equilibrated with acetate buffer (10 mM sodium acetate, 0.1 M NaCl, 2 mM EDTA and 0.02% sodium azide at pH 5) and run at 1 ml/min. The void volume fractions were pooled. Ellman's reagent (G. L. Ellman, *Arch Biochem & Biophys.*, 82:70 (1959)) was used to determine that the peptide was reduced to a thiol.

C: Coupling of peptide to Tetanus toxoid:

Six ml of the reduced peptide was added to 0.3 ml of TT labeled with N-hydroxysuccinimidyl iodoacetate and 1 ml 5×HEPES buffer. After overnight incubation at 4° C., the conjugate was concentrated to about 1 ml using a Macrosep™ 50 device, then desalted into HEPES buffer using P6 cartridges, concentrated again (Macrosep™ 50), and, finally, filtered through a 0.45 micron Millex™ HV filter (Millipore). Evaluation of the protein content using the BioRad assay- showed total protein content to be about 2.6 mg/ml.

Monoclonal Antibody Production:

A: Preparation of anticonsensus peptide monoclonal antibody:

Six BALB/c mice identified as numbers 8378–8383, were immunized with the consensus peptide-TT conjugate. On designated day 1, each mouse was injected subcutaneously with 25 µg conjugate in 0.2 ml emulsified in 60% complete Freund's adjuvant. On day 23, a serum sample was obtained from each mouse. On day 35, all mice except #8382 received a boost of 10 µg consensus peptide conjugate in 0.2 ml 60% incomplete Freund's adjuvant. Mouse 8382 was given 10 µg conjugate of the peptide in 0.1 ml phosphate-buffered saline (PBS).

On day 37, mouse 8382 was used for fusion (96–104). This fusion did not result in production of a monoclonal anti-consensus peptide.

On day 82, the mice received booster immunizations of 10 µg consensus peptide conjugate in 0.2 ml emulsified in 60% incomplete Freund's adjuvant.

On day 85, the spleen from mouse # 8383 was fused with FOX-NY myeloma wherein the myeloma population viability was 97.4%. $1.36 \times 10^8$ spleen cells were fused with $1.37 \times 10^7$ myeloma cells, using PEG (1400 molecular weight) as a fusogen. The hybridomas were assigned culture number 96–109.

Hybridomas were planted into 8 96-well tissue culture dishes with 100 μl/well in RPMI 1640 supplemented with 10% heat-inactivated fetal bovine serum, 10% Hybridoma Serum Free Media (SFM), 100 μM hypoxanthine and 16 μM thymidine (the hypoxanthine and thymidine combination being referred to herein as HT). Eight wells were also planted with FOX-NY myeloma cells only (no hybridomas) as a control. All samples were incubated at 37° C. in a humidified atmosphere of 5% $Co_2$ in air. After 24 hours, all wells received 100 μl RPMI 1640 supplemented with 10% heat-inactivated fetal bovine serum, 10% hybridoma SFM, 200 μM hypoxanthine, 0.8 μM aminopterin and 32 μM thymidine. (The hypoxanthine, aminopterin and thymidine combination being referred to herein as HAT.)

Approximately 96 hours after the fusion, the FOX-NY myelomas in control wells appeared to be dead. Many other wells contained growing colonies of hybridomas seven days after fusion. The growing cells were fed by addition of RPMI 1640 supplemented with 10% heat-inactivated fetal bovine serum, 10% hybridoma SFM and HT. Four days thereafter, the supernatants were tested for the presence of anti-consensus peptide antibodies.

For analysis of peptide binding, an ELISA was used. Nunc MaxIsorp™ stripwells were coated overnight at room temperature with 100 μl/well of consensus peptide at 1 Mg/ml PBS. The wells were then washed four times with PBS containing 0.05% TWEEN-20 ™(PBS-T) to remove unbound material. Each well then received 50 μl of PBS-T. Fifty μl of supernatant was then transferred from the cell culture plate to the corresponding wells of the immunoassay dish. Prior to the transfer of the cell culture, wells were screened microscopically to identify wells without hybridomas. One such well from each plate was used as a background control by substituting PBS-T or medium for the culture supernatant. The plates were then sealed and incubated for 30 to 60 minutes at room temperature in the dark in a draft-free environment. The wells were thereafter washed four times with PBS-T to remove unbound material. Each well then received 95 μl of sheep anti-mouse IgG-HRP (horse radish peroxidase), diluted 1:10000 in PBS-T. Following a 30 minute incubation, the wells were again washed and each well received 100 μl of tetramethylbenzidine (TMB) substrate solution. The plates were then incubated in the dark for 15 minutes at room temperature, after which the reactions were stopped by addition of 80 μl of TMB Stop Solution. The absorbance of each well was determined at 450 mn using a Molecular Devices microplate reader.

Absorbance values for 32 of the supernatants from wells with growing hybridomas was greater than 0.200 units. Of these, only two wells, designated CA8 (1.743) and FE8 (1.092) had absorbance values of greater than 1.000. All thirty-two cultures were expanded by transfer into 24-well culture dishes and grown on RPMI 1640 with 10% FBS. Upon retest, only colony FE8 continued to produce antibodies reactive with the consensus peptide. This culture was expanded to growth in a T75 culture flask and samples were cryopreserved.

The isotype of the antibody secreted by 96-109FE8 was determined using a Zymed isotype kit. The results indicated that the antibody was an IgM with a kappa light chain. The 96-109FE8 culture was cloned into 96-well culture dishes by diluting the cells to a concentration of 4.5–5 cells/ml in RPMI 1640 with 20% FBS and 10% hybridoma SFM. Each well received 200 μl of the cell suspension. Each well was checked for the presence of a single focus of growing hybridomas. The supernatants from each such well were tested for binding of the antibody to the consensus peptide epitope. All of the supernatants were active, suggesting that all of the surviving cells in the original culture were secretors of the antibody of interest, and that the genotype was stable. One clone, designated 96–109FE8 IH11, was expanded, cryopreserved and used in the production of ascites.

Testing of hybridoma tissue culture supernatant for agglutinating activity:

Bacterial culture: ETEC strains bearing the colonization factors CFA/I, CS1, CS2 and CS4 were grown overnight at 37° C. on colonization factor antigen agar [10 gm Casamino acids, 1% (Difco Laboratories, Detroit, Mich.); 1.5 gm yeast extract (Difco), 0.15%; 0.1 gm $MgSO_4.7H_2O$), 0.005% (Sigma, St. Louis); 0.008 gm $MnCl_2$, 0,0005% $MnCl_2$ (Sigma); 20 gm agar (Difco);, q.s. to 1 liter with deionized water]. Those ETEC strains bearing the colonization factors CS17 and PCF 0166 are also grown on colonization factor antigen agar, which was also supplemented with 0.15% bile salts (bile salts #3, Difco). Bacteria were harvested into phosphate buffer saline (PBS) solution and the concentration of bacterial suspension was adjusted to an optical density of 20 (when diluted 1/20 gives an OD of 1.00+/–0.005 at 600 nm). Bacterial culture supernatant tant was tested at full strength or serially diluted 1:2 with PBS.

The following assay was used: Eight μl of bacterial suspension was mixed with an equal volume of tissue culture supernatant dilution on a glass microscope slide (25×75 mm) at room temperature. In a separate place on the same slide there is a control consisting of bacterial suspension with 8 μl of PBS (autoagglutination control). The mixture is rocked back and forth continuously and the agglutination is observed at 10 seconds, 30 seconds, 1 minute and 2 minutes. The results are visually scored as follows:

4 =agglutination in less than 10 seconds with large clumps
3 =agglutination in less than 30 seconds with large clumps
2 =agglutination in less than 60 seconds with medium clumps
1 =agglutination in less than 2 minutes with small clumps
0 =no agglutination within 2 minutes.

Results:

At undiluted tissue culture supernatant (estimated at 1 μg/ml of antibody), no bacterial strains were agglutinated. After concentration of tissue culture supernatant to 20 fold concentration (YM 100 centrifugal ultrafilter, Amicon, Danvers, Mass.), only the bacterial strain expressing CFA/I was agglutinated (HI0407NM). The monoclonal antibody supernatant was then concentrated 130 fold from original strength and tested. Under these circumstances, the antibody agglutinated all bacteria bearing CS4-CFA/I family proteins.

The hybridoma identified as 96-109FE8 IH11 has been deposited in the American Type Culture Collection at 10801 University Boulevard, Manasses, Va. 20110-2209and given the designation ATCC HB-12163deposited Aug. 9, 1996.

As indicated above the antibody may be used for purposes of identifying *E. coli* bearing the CS4-CFA/I protein family. The samples suspected of containing *E. coli* of the CS4-CFA/I protein may be grown by usual methods in the clinical laboratory. The colonies of organisms may then be suspended by the method disclosed above. The suspended organisms are then exposed to a composition containing at least 30 μg/ml of antibody. In a preferred embodiment, the suspended organisms would be exposed to a composition containing an antibody concentration of 100 to 130 μg/ml. Appropriate samples would include stools from patients suffering from diarrhea and for testing food and environmental samples for contamination with ETEC *E. coli* organisms.

The monoclonal antibody (MAB) is useful for identifying members of the CS4-CFA/I family in cultures. Assay kits containing the MAB may be prepared and may contain, in addition to the MAB of the invention, agents for tagging for facilitate identification of the MAB/antigen complex. Such tags include -radioactive isotopes, fluorescing agents and colorometric indicators. Such agents may be attached to solid supports. For example, an ELISA test kit system may be used to identify the MAB/antigen complex.

Compositions containing the MAB of the invention may be prepared using as a carrier appropriate for addition to a growth media. Saline and other buffered solutions known in the art are appropriate as carriers for the MAB.

MABs of the invention may also be prepared in pharmaceutically acceptable carrier solutions and may be administered to the infected area to agglutinate the bacteria bearing CS4-CFA/I proteins. Administration would provide means for the compositions to contact the organisms. For example, the compositions could be administred orally in capsules which protect the antibody from destruction in the stomach and duedenum. The compositions are appropriate for use both for short-term prophylaxis and for treatment of ETEC *E. coli* infections by administration of an ETEC *E. coli* agglutinating effective amount of the pharmaceutical composition.

What is claimed is:

1. A monoclonal antibody produced by hybridoma deposited as ATCC HB-12163 which agglutinates bacteria bearing CS4-CFA/I family of proteins and binds exclusively and specifically to amino acid sequence SAVALTYS (SEQ ID NO. 2).

2. A composition comprising the monoclonal antibody of claim 1 in a carrier appropriate for application to a bacteria-containing growth media.

3. The composition of claim 2 wherein the monoclonal antibody has a tag to assist in identification of an antibody/CS4-CFA/I protein complex.

4. The composition of claim 3 wherein the tag is a colorometric tag.

5. The composition of claim 3 wherein the tag is a fluorescing agent.

6. A composition comprising the antibody of claim 1 in a pharmaceutically acceptable carrier.

7. The composition of claim 6 wherein the carrier is saline.

* * * * *